(12) United States Patent
Kerr

(10) Patent No.: US 9,161,812 B2
(45) Date of Patent: Oct. 20, 2015

(54) FINGER-MOUNTABLE ABLATION DEVICE

(71) Applicant: Covidien LP, Mansfield, MA (US)

(72) Inventor: Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 156 days.

(21) Appl. No.: 13/803,762

(22) Filed: Mar. 14, 2013

(65) Prior Publication Data

US 2014/0025059 A1    Jan. 23, 2014

Related U.S. Application Data

(60) Provisional application No. 61/673,651, filed on Jul. 19, 2012.

(51) Int. Cl.

| | | |
|---|---|---|
| *A61B 18/18* | (2006.01) | |
| *A61B 5/04* | (2006.01) | |
| *A61N 1/00* | (2006.01) | |
| *A61B 18/14* | (2006.01) | |
| *A61B 17/00* | (2006.01) | |
| *A61B 18/00* | (2006.01) | |
| *A61B 19/00* | (2006.01) | |

(52) U.S. Cl.
CPC .............. *A61B 18/18* (2013.01); *A61B 18/14* (2013.01); *A61B 2017/00057* (2013.01); *A61B 2017/00061* (2013.01); *A61B 2017/00084* (2013.01); *A61B 2017/00345* (2013.01); *A61B 2017/00438* (2013.01); *A61B 2018/00791* (2013.01); *A61B 2019/261* (2013.01); *A61B 2019/464* (2013.01); *A61B 2019/465* (2013.01); *A61B 2562/0266* (2013.01)

(58) Field of Classification Search
USPC ............................................ 607/112; 600/485
See application file for complete search history.

(56) References Cited

U.S. PATENT DOCUMENTS

| | | | |
|---|---|---|---|
| 7,089,061 B2 * | 8/2006 | Grey | 607/63 |
| 7,393,354 B2 | 7/2008 | Buchman, II et al. | |
| 7,553,686 B2 | 6/2009 | George et al. | |
| 2006/0224053 A1 | 10/2006 | Black et al. | |
| 2007/0276262 A1 * | 11/2007 | Banet et al. | 600/485 |
| 2008/0077200 A1 | 3/2008 | Bendett et al. | |
| 2008/0125775 A1 | 5/2008 | Morris | |
| 2012/0296317 A1 | 11/2012 | Chernov et al. | |
| 2012/0296323 A1 | 11/2012 | Chernov et al. | |
| 2012/0296324 A1 | 11/2012 | Chernov et al. | |

* cited by examiner

*Primary Examiner* — Nicole F Lavert

(57) ABSTRACT

A surgical device is disclosed, and includes a pair of finger-mountable annular members, each having an electrode disposed thereon. An optical member is disposed on at least one of the pair of finger-mountable annular members and has a first set of light transmitting properties corresponding to a first set of physical parameters of at least one of the finger-mountable annular members. At least one finger-mountable annular member is configured to transition to a second set of physical parameters being different from the first set of physical parameters. The optical member is configured to transition from a first set of light transmitting properties to a second set of light transmitting properties, the second set of light transmitting properties corresponding to the second set of physical parameters, the second set of light transmitting properties being different from the first set of light transmitting properties.

16 Claims, 6 Drawing Sheets

FINGER-MOUNTABLE ABLATION DEVICE

CROSS REFERENCE TO RELATED APPLICATION

The present application claims the benefit of and priority to U.S. Provisional Application Ser. No. 61/673,651, filed on Jul. 19, 2012, the entire contents of which are incorporated herein by reference.

BACKGROUND

1. Technical Field

The present disclosure relates generally to an electrosurgical device, and more particularly to one or more finger-mountable annular members including an electrode for treating tissue and an optical fiber for the detection of the changing physical characteristics of the finger-mountable annular member.

2. Background of Related Art

Electrosurgical instruments are commonly used in open and minimally invasive surgical procedures. Because nerve and muscle stimulation cease at 100,000 cycles per second (100 kHz), electrosurgical procedures can be performed safely at radio frequencies ("RF") above 100 kHz. At these frequencies, electrosurgical energy can pass through a patient with minimal neuromuscular stimulation.

Electrosurgery involves application of high RF electrical current to a surgical site to cut, ablate, or coagulate tissue. In monopolar electrosurgery, a source or active electrode delivers RF energy from the electrosurgical generator to the tissue and a return electrode carries the current back to the generator. The source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes, e.g., electrosurgical forceps, graspers, pencils, and the like. In this manner, the applied electrical current is limited to the body tissue positioned between the electrodes. When the electrodes are sufficiently separated from one another, the electrical circuit is open and thus incidental contact of body tissue with either of the separated electrodes inhibits current flow.

Bipolar electrosurgical instruments often include opposed electrodes disposed on opposing tissue engaging faces of a pair of cooperating members such as jaws, graspers, or plates. The electrodes are charged to opposite electrical potentials such that an electrosurgical current may be selectively transferred through tissue grasped between the electrodes. However, electrosurgical instruments often have a limited range of motion, e.g., due to mechanical design constraints. This limited range of motion may be disadvantageous to a surgeon working in an area that requires a complex series of movements. In such situations, it may be desirable to use electrosurgical instruments that facilitate a wide and variable range of motion to allow for complex surgical articulation. Thus, the mechanical nature of some electrosurgical instruments may limit the amount of tactile sensory feedback received by the surgeon during a procedure. In certain procedures, it may be useful to have the ability to determine how much pressure to apply to a coagulation, cutting, or sealing surface.

SUMMARY

It would be desirable to provide a more dexterous electrosurgical instrument for facilitating complex motions during an endoscopic or endoluminal procedure. It would further be desirable to provide such an instrument having the capability to provide feedback to an operator on the performance and the condition of the electrosurgical device and surrounding tissue, e.g., temperature, mechanical strain, and other relevant characteristics.

The present disclosure relates to an electrosurgical apparatus and methods for performing electrosurgical procedures. More particularly, the present disclosure relates to electrosurgically coagulating and sealing tissue. As is traditional, the term "distal" refers herein to an end of a device that is farther from an operator, and the term "proximal" refers herein to the end of a device which is closer to the operator. In further aspects of the present disclosure, "distal" may refer to an end or portion of a device closest to an operator's fingertip, and "proximal" may refer to an end or portion of a device furthest from an operator's fingertip.

As used herein, "bipolar" electrosurgery involves one of a pair of electrodes functioning as an active electrode and the other electrode functioning as a return electrode. The return electrode is placed in close proximity to the active electrode such that an electrical circuit is formed between the two electrodes.

Further, "monopolar" electrosurgery involves the use of a source or active electrode to deliver RF energy from an electrosurgical generator to tissue and a return electrode carries the current back to the electrosurgical generator. A patient return electrode is placed remotely from the active electrode to carry the current back to the generator.

As described herein, electrosurgical tissue sealing may include electrosurgical fulguration. Electrosurgical fulgration comprises the application of an electric spark to biological tissue, for example, human flesh or the tissue of internal organs, without significant cutting. The spark is produced by bursts of RF electrical energy generated from an appropriate electrosurgical generator. Generally, fulguration is used to dehydrate, shrink, necrose, or char the tissue. As a result, the instrument is primarily used to stop bleeding and oozing. These operations are generically embraced by the term "coagulation". Meanwhile, electrosurgical cutting includes the use of the applied electric spark to tissue which produces a cutting effect. Electrosurgical sealing includes utilizing both electrosurgical energy and pressure to melt the tissue collagen into a fused mass.

According to one aspect of the present disclosure, a surgical device includes a pair of finger-mountable annular members, each having an electrode disposed thereon. An optical member is disposed on at least one of the finger-mountable annular members and has a first set of light transmitting properties corresponding to a first set of physical parameters of at least one of the finger-mountable annular members. At least one finger-mountable annular member is configured to transition to a second set of physical parameters, the second set of physical parameters being different from the first set of physical parameters. The optical member is configured to transition from a first set of light transmitting properties to a second set of light transmitting properties, the second set of light transmitting properties corresponding to the second set of physical parameters being different from the first set of light transmitting properties.

In a further aspect of the present disclosure, the first and second sets of physical parameters are selected from the group consisting of temperature and mechanical strain. The first and second sets of light transmitting properties may include transmittance.

According to another aspect of the present disclosure, a surgical device includes a first finger-mountable annular member and a second finger-mountable annular member, each of the first and second finger-mountable annular members including a tissue engaging surface, the tissue engaging surfaces of the respective first and second finger-mountable annular members spaced away from each other in opposed relation. An electrode is disposed on each of the respective tissue engaging surfaces, and each electrode is configured to be coupled to an electrosurgical generator. A sensor assembly is operably coupled to at least one of the first finger-mountable annular member and the second finger-mountable annular member, and includes an optical member and a light source, the optical member configured to transmit light from the light source. A change in the transmission of light through the optical member corresponds to a changed condition of at least one of the first and second finger-mountable annular members.

In another aspect of the present disclosure, each of the first and second finger-mountable annular members defines an opening therethrough. The opening of each of the first and second finger-mountable annular members may be configured to engage a mountable member.

In a further aspect of the present disclosure, the changed condition of at least one of the first and second finger-mountable annular members includes at least one of a change in temperature and a change in mechanical strain.

In yet a further aspect of the present disclosure the optical member is associated with the first finger-mountable annular member, and a second optical member is associated with the second finger-mountable annular member. The optical member is at least partially disposed within a portion of one of the first and second finger-mountable annular members.

In another aspect of the present disclosure, the optical member may include a fiber Bragg grating. The fiber Bragg grating may reflect a first wavelength of light transmitted from the light source. In the changed condition, the fiber Bragg grating may reflect a second wavelength of light from the light source, the second wavelength of light being different from the first wavelength of light. The fiber Bragg grating may include a plurality of segments disposed in a periodic pattern, and each of the plurality of segments has a predetermined refractive index.

In a further aspect of the present disclosure, the optical member defines a length and has a refractive index that varies along the length of the optical member.

In yet another aspect of the present disclosure, each of the electrodes is configured to pass a current therebetween.

A further aspect of the present disclosure describes a method of measuring strain through an electrosurgical device, and includes providing an electrosurgical device having a pair of electrodes supported on a respective pair of finger-mountable annular members, at least one of the finger-mountable annular members including a light transmissive member, the light transmissive member including a spaced plurality of segments configured to reflect at least one wavelength of light and transmit at least one wavelength of light. The method further includes projecting light through the light transmissive member and measuring a first wavelength of light transmitted through the light transmissive member. The method additionally includes forcing the pair of finger-mountable annular members into contact such that a force is exerted on the light transmissive member, the force causing a change in spacing between the plurality of segments, and measuring a second wavelength of light transmitted through the light transmissive member after the force is applied. The method also includes comparing the first wavelength of light to the second wavelength of light to determine a change in spacing between the plurality of segments resulting from the force.

In a further aspect of the present disclosure, the step of comparing the first wavelength of light to the second wavelength of light includes determining the amount of strain experienced by one of the finger-mountable annular members including the light transmissive member.

In another aspect of the present disclosure, the step of providing an electrosurgical device includes supplying a current between the pair of electrodes. In a further aspect of the present disclosure, the method further includes the step of engaging a section of tissue such that the section of tissue is disposed between the pair of finger-mountable annular members.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

The present disclosure provides for a system and method for providing a variety of sensor feedback regarding operation of an electrosurgical device including a pair of finger-mountable annular members including, but not limited to, temperature of the finger-mountable annular members and the surrounding tissue, pressure exerted on the finger-mountable annular members, position and pressure of various mechanical components of the electrosurgical device, and identification information corresponding to the electrosurgical device. Although the feedback system according to present disclosure is described below with respect to a pair of finger-mountable annular members, the system may be utilized in a variety of surgical instruments, including but not limited to, open surgical forceps, tweezer-type devices, graspers, staplers, pencils, needles, and the like. Although this configuration is typically associated with instruments for use in laparoscopic or endoscopic surgical procedures, various aspects of the present disclosure may be practiced with traditional open instruments and in connection with endoluminal procedures as well.

Figure 1:
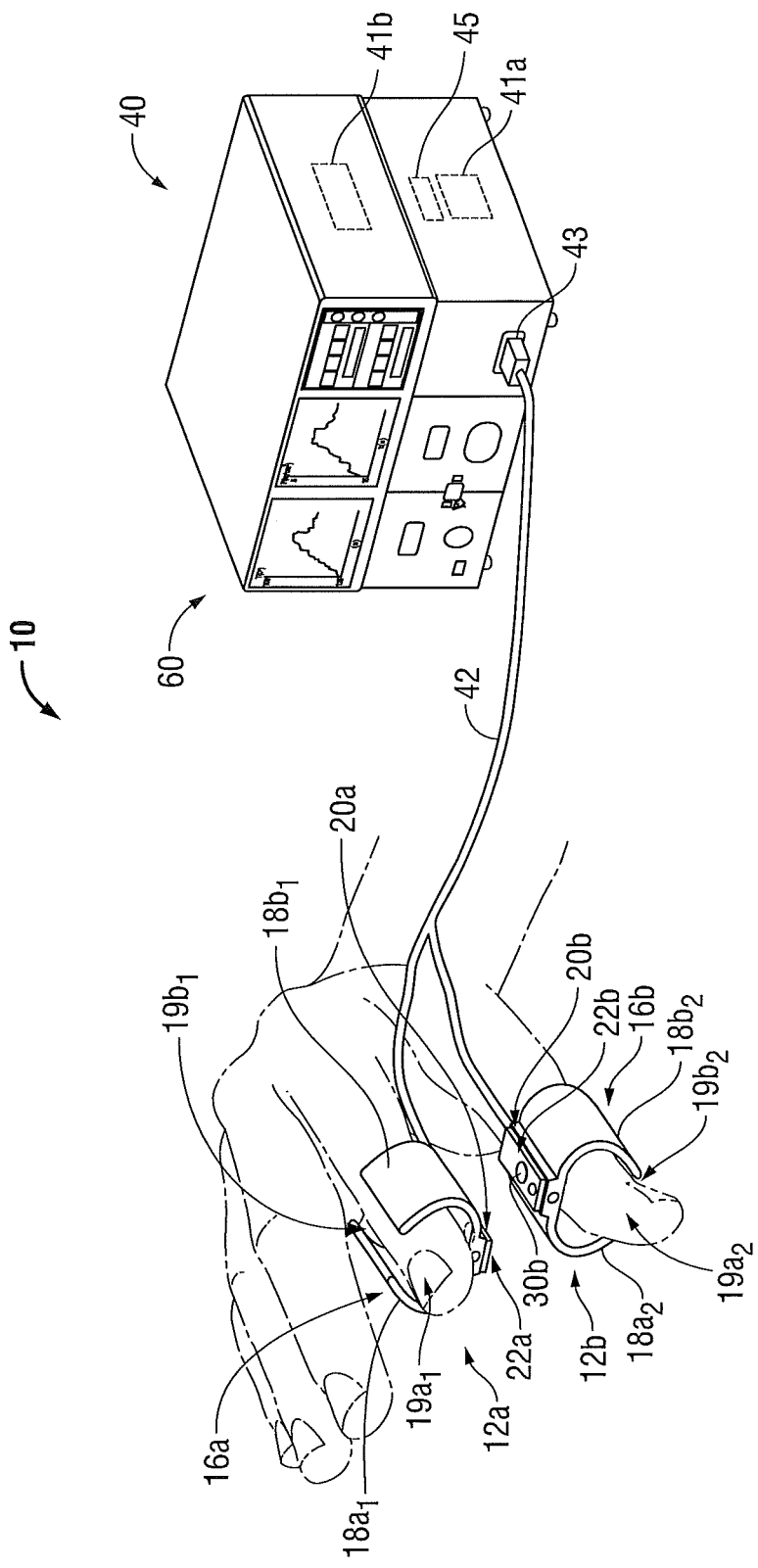
FIG. 1 is a perspective view of an embodiment of an electrosurgical device according to the present disclosure.

With reference to FIG. 1, an embodiment of an electrosurgical device 10 is shown, and includes a pair of finger-mountable annular members 12*a*, 12*b* that are electrically coupled with a source of electrosurgical energy such as electrosurgical generator 40. The generator 40 may be any suitable generator such as the LIGASURE® Vessel Sealing Generator and the FORCETRIAD® Generator sold by Surgical Solutions of Boulder, Colo. Other suitable electrosurgical generators as are known in the art may be used with electrosurgical device 10. The generator 40 includes a display system 60, which may be integrally formed with the generator 40, e.g., disposed in the same housing, and will be described in further detail below.

A cable 42 extends between each finger-mountable annular member 12 and the generator 40. Accordingly, cable 42 may be split between each finger-mountable annular member 12a, 12b and joined approaching generator 40. A connector 43 is disposed on an end of the cable 42 and interfaces with generator 40 such that the finger-mountable annular members 12a, 12b may be selectively coupled and decoupled electrically from the generator 40. In some embodiments, the cable 42 includes additional connectors 43 such that finger-mountable annular members 12a, 12b may be selectively coupled or decoupled to the cable 42 in this manner.

As shown, each finger-mountable annular member 12a, 12b includes a mounting portion 16a, 16b and a tissue engaging portion 20a, 20b, respectively. The finger-mountable annular members 12a, 12b, as shown, may be spaced apart in opposed relation on an operator's index finger and thumb. In some embodiments, finger-mountable annular members 12a, 12b may be engaged by other combinations of an operator's digits, or may be configured to engage a driving mechanism, such as a robotic arm or mechanical actuator.

Mounting portions 16a, 16b as shown are configured as substantially C-shaped or open cylindrical members. A respective pair of arcuate members $18a_1$, $18b_1$ and $18a_2$, $18b_2$, extend from a proximal portion of the tissue engaging portions 20a, 20b, defining openings $19a_1$, $19b_1$. Arcuate members $18a_1$, $18b_1$ and $18a_2$, $18b_2$ are curved in a manner so as to approach a respective circumferential gap $19b_1$, $19b_2$. The openings $19a_1$, $19a_2$ and the gaps $19b_1$, $19b_2$ permit the insertion of a mountable member, such as a portion of an operator's finger, as shown. Accordingly, arcuate members $18a_1$, $18b_1$ and $18a_2$, $18b_2$ may be resilient or flexible and configured to radially flex in tension to widen gaps $19b_1$, $19b_2$ for the reception of a respective mountable member. Suitable materials for arcuate members $18a_1$, $18b_1$ and $18a_2$, $18b_2$ may include, but are not limited to, metal, polymeric materials, and composites. In some embodiments, openings $19a_1$, $19a_2$ may be shaped, dimensioned, or otherwise configured to receive any number of operator's digits or a driving mechanism, as described above. In further embodiments, mounting portions 16a, 16b may be any suitable shape, such as a loop or ring configuration, a conical sleeve with a closed distal end, or an open circular frame configured and dimensioned to fit around a finger. Those skilled in the art of the present disclosure will envision other suitable configurations and arrangements for mounting portions 16a, 16b.

Tissue engaging portions 20a, 20b are exposed on a distally-facing surface of the respective mounting portions 16a, 16b. A tissue engaging surface 22a, 22b is defined on each respective tissue engaging portion 20a, 20b and may have surface features for engagement with a section of tissue "T" (FIG. 5), such as knurls, grooves, spikes, or the like. In some embodiments, the finger-mountable annular members 12a, 12b are oriented such that the respective tissue engaging surfaces 22a, 22b are exposed facing away from an operator's finger pad. In some embodiments, tissue engaging surfaces 22a, 22b may have an arcuate or otherwise contoured profile for engagement with like-shaped tissue sections. The tissue engaging portions 20a, 20b may be attached to or integrally formed with the mounting portions 16a, 16b. In further embodiments, tissue engaging portions 20a, 20b may be snap-fit, adhered, secured with sutures or another binding member, or ultrasonically welded to mounting portions 16a, 16b. One skilled in the art of the present disclosure will envision other suitable coupling between mounting portion 16a, 16b and tissue engaging portions 20a, 20b.

One or more electrodes 30a (FIG. 5), 30b are disposed on each respective tissue engaging surface 22a, 22b of the finger-mountable annular members 12a, 12b. Electrodes 30a, 30b may be attached to respective tissue engaging surfaces 22a, 22b, or may be partially recessed within and protrude from the tissue engaging surfaces 22a, 22b. In some embodiments, each entire tissue engaging surface 22a, 22b may be configured as an electrode. The electrodes 30a, 30b may be fabricated from any electrically-conductive material or may be coated with an electrically conductive material, e.g., stainless steel, aluminum, platinum, titanium, copper, gold or silver. Electrodes 30a, 30b may be connected to the generator 40 through cable 42, or may be directly connected to the generator 40 through separate transmission lines (not shown). In some embodiments, transmission lines or a portion of cable 42 may be integrally formed with or disposed within a channel defined in the finger-mountable annular members 12a, 12b, as will be described in further detail below.

One or more fibers $500a_1$, $500b_1$ and $500a_2$, $500b_2$ (FIGS. 5-6) are associated with electrosurgical device 10. Fibers $500a_1$, $500b_1$ and $500a_2$, $500b_2$ may be optical sense fibers, such as phosphate glass fibers, or may be any suitable type of light transmissive member. Fibers $500a_1$, $500b_1$ and $500a_2$, $500b_2$ may be disposed on, within or attached to one or both finger-mountable annular members 12a, 12b, as will be described further below.

Fibers $500a_1$, $500b_1$ and $500a_2$, $500b_2$ are configured to sense one or more sets of physical parameters, e.g., temperature and mechanical strain, within the finger-mountable annular members 12a, 12b and other components of the electrosurgical device 10 and may provide identification information of the finger-mountable annular members 12a, 12b to the generator 40. In this manner, fibers $500a_1$, $500b_1$ and $500a_2$, $500b_2$ act as a sensor assembly, and may be coupled with a light source. The generator 40 also includes an interrogator 41a (FIG. 1) coupled to the fibers $500a_1$, $500b_1$ and $500a_2$, $500b_2$ that decodes the optically encoded strain information from fibers $500a_1$, $500b_1$ and $500a_2$, $500b_2$ into electrical signals compatible with the computer control hardware of the generator 40. The generator 40 includes a controller 41b, which is used to calculate temperature and forces exerted on the fibers $500a_1$, $500b_1$ and $500a_2$, $500b_2$, as described in further detail below. The controller 41b may be any suitable type of logic circuit, such as field programmable gate array, processor, and the like. The generator 40 also includes a receptacle 45 (FIG. 1) configured to interface with the connector 43.

Figure 2:
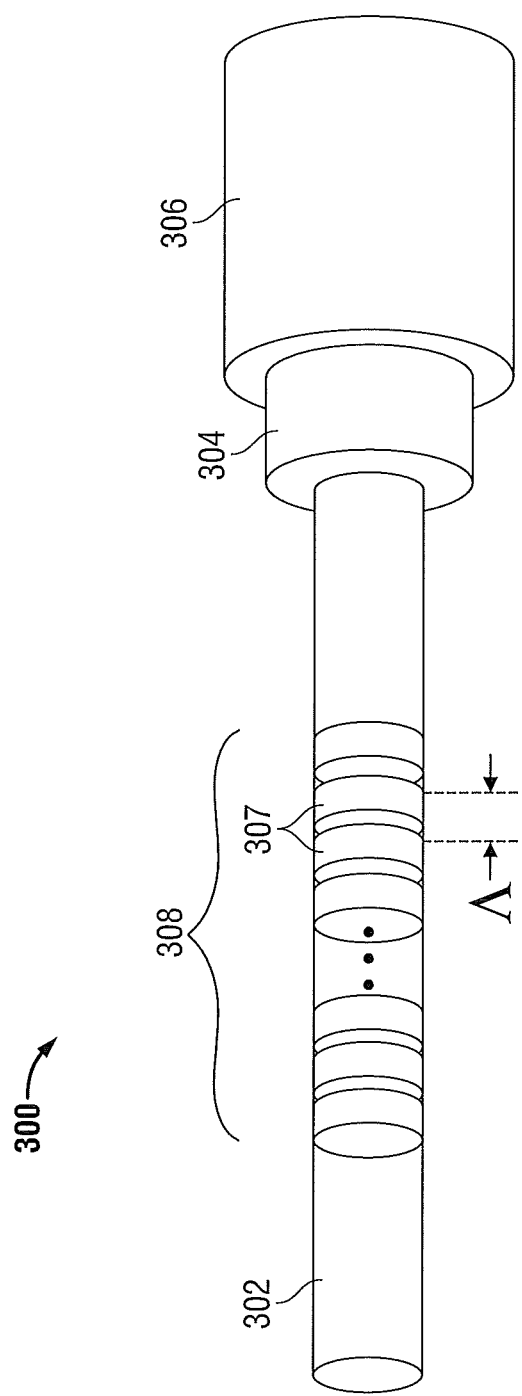
FIG. 2 is a perspective view of an optical fiber according to the present disclosure.

With reference now to FIG. 2, the fibers $500a_1$, $500b_1$ and $500a_2$, $500b_2$ and fiber 400 are described with respect to a fiber 300 to avoid repetition. The fiber 300 includes a core 302, a cladding 304 disposed over the core 302, and a buffer coating 306 covering the cladding 304. The fiber 300 also includes one or more fiber Bragg gratings (FBG) 308. Multiple gratings 308 may be written, e.g., etched, into the fiber 300 if the gratings 308 are formed in such a way as to use different wavelengths. This is particularly useful for using a single fiber to sense multiple locations within the instrument. In further embodiments, multiple fibers 300 may be included each having one or more gratings 308.

The gratings 308 include a plurality of reflection points 307 written into the fiber 300 at periodic spacing "Λ." In some embodiments, the grating 308 may be written into the fiber 300 using high intensity pulses from a laser (e.g., argon fluoride excimer laser with a phase mask). As the fiber 300 undergoes mechanical strain (e.g., a change in length) due to temperature and pressure changes, the spacing Λ is modified due to stretching or contraction of the fiber 300. The effects of strain and temperature are quantified by measuring the wavelength shift in light reflected by the reflection points 307 based on the formula (I), which is reproduced below:

$$\frac{\Delta\lambda}{\lambda_0} = k * \varepsilon + \alpha_\delta * \Delta T \quad (I)$$

In formula (I), Δλ is the wavelength shift, $\lambda_0$ is the base wavelength, k is a gage factor, which is a difference between 1 and a photo-elastic coefficient, ρ, ε is strain, ΔT is a temperature change, and $\alpha_\delta$ is a change of the refraction index.

In this manner, the light transmissive properties, namely transmittance, of the fiber 300 corresponds to a set of physical parameters of the finger-mountable annular members 12a, 12b (FIG. 1). The light transmissive properties of the fiber 300 may transition with changing physical parameters of the finger-mountable annular members 12a, 12b.

Figure 3:
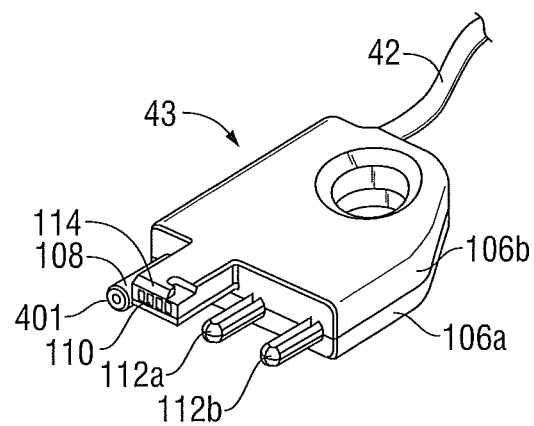
FIG. 3 is a perspective view of a connector according to an embodiment of the present disclosure.
Figure 4:
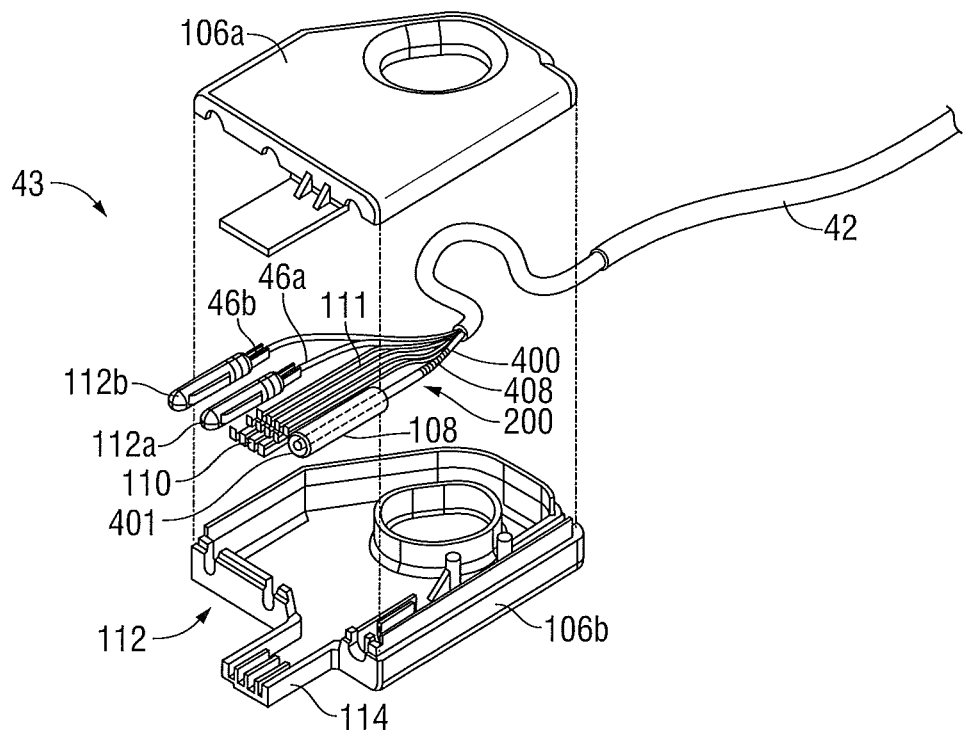
FIG. 4 is an exploded, perspective view of the connector of FIG. 4 according to an embodiment of the present disclosure.

With additional reference to FIGS. 3 and 4, an embodiment of connector 43 is shown coupled to cable 42 and includes a housing portion 106 having a first-half section 106a and a second half-section 106b operatively engagable with one another. Half-sections 106a, 106b are configured to retain an active pin 112a, a return pin 112b, an optical coupler 108, and a plurality of electrical contacts 110 disposed on a prong 114. The pin 112a is coupled to the wire 46a and the pin 112b is coupled to the wire 46b. The electrical contacts 110 are coupled to control leads 111, which may be coupled to various electrical controls, e.g., switch 36. The optical coupler 108 is connected to a fiber 400 at a proximal end 401 of the fiber 400. Fiber 400 is substantially similar to fiber 300 discussed above. The receptacle 45 includes corresponding connectors for coupling the pins 112a, 112b, contacts 110, and optical coupler 108 to the generator 40, namely, energy-generating components (e.g., RF output stage), sensor circuits, the interrogator 41a, and the controller 41b.

The connector 43 includes an identification assembly 200 including the fiber 400, which includes a fiber Bragg grating 408 at a proximal end 401 thereof. The proximal end 401 of the optical fiber 400 that includes the fiber Bragg grating 408 is mounted loosely within the housing 106 of the connector 43 such that strain does not transfer to the fiber 400. In some embodiments, the fiber 400 may be thermally insulated (e.g., potting of the housing 106) to prevent thermal effects of the fiber Bragg grating 408. This configuration allows the fiber Bragg grating 408 to be unaffected by thermal and strain imposed on the connector 43. Accordingly, the fiber Bragg grating 408 provides the same feedback when interrogated by the interrogator 41a. The fiber Bragg grating 408 may be individually tailored to encode identification information corresponding to a specific device (e.g., finger-mountable annular members 12a, 12b). The identification information that may be encoded in the fiber Bragg grating 408 may include, but is not limited to, serial number, model number, usage settings, configuration settings, and the like. Different identification information may be encoded by varying the number, thickness and periodic spacing between reflection points of the fiber Bragg grating 408. The interrogator 41a may interrogate the identification assembly 200 upon insertion of the connector 43 into the receptacle 45. Interrogation may be triggered by detection of the insertion using one or more proximity switches, limit switches, radio frequency tags, and the like.

Figure 5:
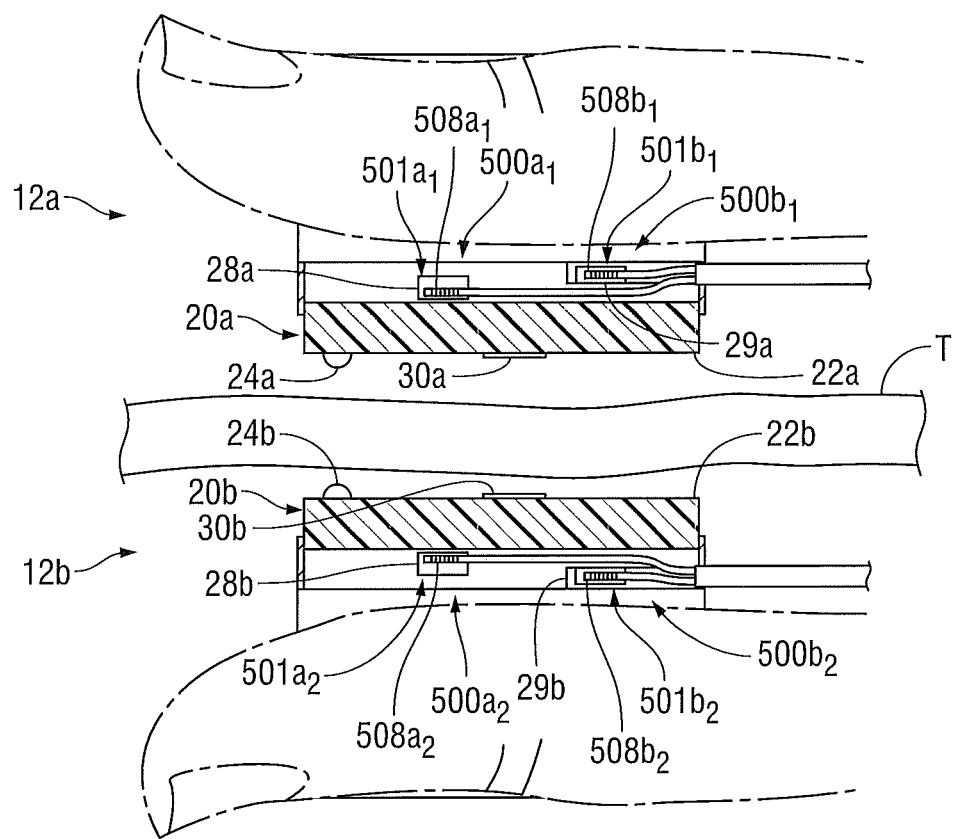
FIG. 5 is a side, cross sectional view of a pair of the finger-mountable annular members of FIG. 1 in a spaced-apart configuration according to the present disclosure.
Figure 6:
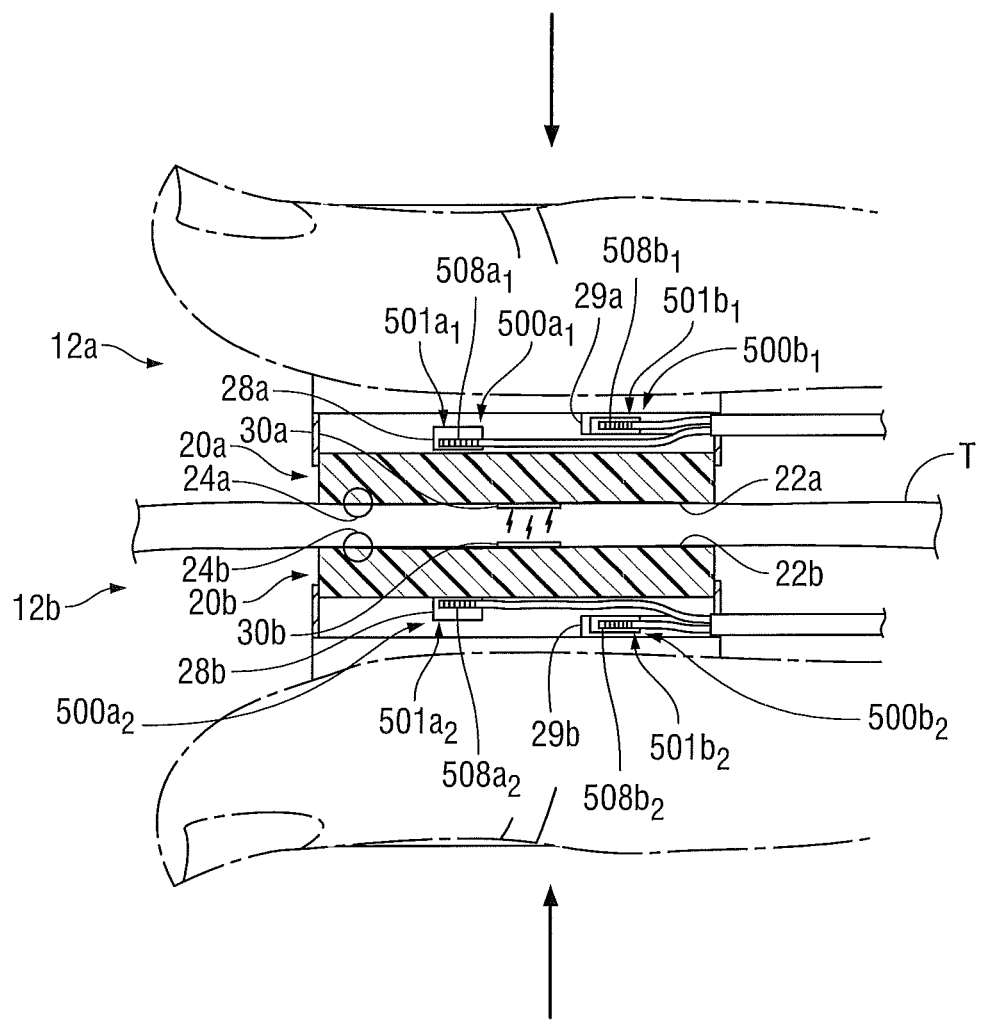
FIG. 6 is a side, cross sectional view of a pair of the finger-mountable annular members of FIG. 1 in an approximated configuration according to the present disclosure.

Referring now to FIGS. 5 and 6, the finger-mountable annular members 12a, 12b may be moved between an open position and spaced apart position (FIG. 5), wherein tissue "T" is received between the finger-mountable annular members 12a, 12b, and a closed or clamped configuration (FIG. 6), wherein the tissue T is clamped and sealed. As described above, finger-mountable annular members 12a, 12b may be engaged with an operator's fingers and subject to a "pinching" movement to effect approximation. As the electrodes 30a, 30b are electrically coupled to cable 42 (FIG. 1), and thus to the generator 40 (FIG. 1), RF energy may be transmitted between electrodes 30a, 30b, as shown. In some embodiments, the opposed tissue engaging surfaces 22a, 22b with the respective electrodes 30a, 30b disposed thereon are electrically coupled to opposite terminals, e.g., active and return terminals, associated with the generator 40. Thus, bipolar energy may be provided through the tissue engaging surfaces 22a, 22b. Alternatively, the tissue engaging surfaces 22a, 22b may be configured for delivering monopolar energy to the tissue "T". In a monopolar configuration, one or both tissue engaging surfaces 22a, 22b deliver electrosurgical energy from an active terminal coupled to one or more of the electrodes 30a, 30b, while a return pad (not shown) is placed generally beneath a patient and provides a return path to the opposite terminal, of the generator 40

As finger-mountable annular members 12a, 12b are approximated to the closed configuration of FIG. 6, the tissue engaging surfaces 22a, 22b may be configured to provide a consistent pressure to tissue T grasped therebetween. To provide a consistent and effective tissue seal, the pressure may be from about 3 kg/cm² to about 16 kg/cm² and, in some embodiments, from about 7 kg/cm² to about 13 kg/cm². As described in further detail below, the pressure being measured by fiber $500a_1$ and/or $500a_2$ is displayed on display 60, allowing the operator to control the grasping pressure. Additionally, an appropriate distance between tissue engaging surfaces 22a, 22b, e.g., from about 0.001 inches to about 0.006 inches should be maintained and, in some embodiments, from about 0.002 inches to about 0.005 inches. In further embodiments, a minimum desired separation or gap distance is maintained between the tissue engaging surfaces 22a, 22b by a stop 24a, 24b or other protrusion formed on one or more of the tissue engaging portions 20a, 20b of finger-mountable annular members 12.

As described above, the opposing finger-mountable annular members 12a, 12b include the respective fibers $500a_1$, $500b_1$ and $500a_2$, $500b_2$. For purposes of simplicity and consistency, use of fibers $500a_1$, $500b_1$ and $500a_2$, $500b_2$ to monitor temperature and pressure are described hereinbelow with reference to finger-mountable annular member 12a only. Accordingly, references to channels 28b, 29b housing the proximal and distal ends $501a_2$, $501b_2$ and Fiber Bragg gratings $508a_2$, $508b_2$ of the respective fibers $500a_2$, $500b_2$ of annular member 12b will not be described. In some embodiments, fibers $500a_1$, $500b_1$ and $500a_2$, $500b_2$ may be disposed within one or more finger-mountable annular members 12a, 12b.

The first fiber $500a_1$ is disposed in a first channel 28a defined through the tissue engaging portion 20a near tissue engaging surface 22a. The second fiber $500b_1$ is disposed in a second channel 29a spaced away from the first channel 28a. The second channel 29a may be disposed within a portion of the arcuate members $18a_1$, $18b_1$ (FIG. 1) or may be disposed within another portion of the finger-mountable annular member 12a spaced away from the channel 29a. In some embodiments, the finger-mountable annular members 12a may be formed or molded about the fibers $500a_1$, $500b_1$.

The fibers $500a_1$, $500b_1$ include distal ends $501a_1$, $501b_1$, respectively, which are disposed within the first and second channels 28a, 29a of the finger-mountable annular member 12a. Each of the fibers $500a_1$, $500b_1$ includes one or more fiber Bragg gratings $508a_1$, $508b_1$ disposed within first and second channels 28a, 29a, respectively. The first and second channels 28a, 29a may be filled with thermally and electrically conductive material. The material may be a liquid, such as saline. When light is projected through fibers $500a_1$, $500b_1$, both of the fiber Bragg gratings $508a_1$, $508b_1$, measure temperature at or near the finger-mountable annular members 12a. The fiber $500a_1$ is securely mounted within the finger-mountable annular member 12a, e.g., glued thereto along the entire length thereof, to provide strain measurements imposed on the finger-mountable annular member 12a. Strain measurements allow for determination of pressure exerted on the finger-mountable annular member 12a. However, the gratings $508a_1$ are affected by both temperature and strain. To obtain accurate strain measurements at the finger-mountable annular member 12a, fiber $500b_1$ is mounted in a less secure manner to finger-mountable annular member 12a (e.g., only at the distal end $501b_1$) such that strain does not transfer to the fiber $500b_1$. This configuration allows the fiber $500b_1$ to be affected only by temperature. Thus, the fiber $500a_1$ provides sensor feedback regarding temperature and strain to the interrogator 41a while the fiber $500b_1$ only provides temperature feedback. The temperature feedback from the fiber $500b_1$ is used by the interrogator 41a and/or the controller 41b to determine the temperature at the finger-mountable annular member 12a and the tissue site, as well as the strain by correcting the feedback from the fiber $500a_1$ using the feedback from the fiber $500b_1$. The feedback signal from the fiber $500b_1$ is used to remove the temperature component of the feedback signal from the fiber $500a_1$ to obtain the strain component. In this manner, measuring a first wavelength of light transmitted through the fibers $500a_1$, $500b_1$, forcing the finger-mountable annular members 12a, 12b into contact such that a force is exerted on the fibers $500a_1$, $500b_1$ causing a change in spacing between the Bragg gratings $508a_1$ $508b_1$, and measuring a second wavelength of light transmitted through the fibers $500a_1$, $500b_1$ allows a comparison of the changed spacing between the Bragg gratings $508a_1$, $508b_1$ indicative of mechanical strain and changed temperature.

The temperature and strain feedback may be used by the controller 41b to control the output of the generator 40. In some embodiments, the adjustments to the output of the generator 40 may include, but are not limited to, changing modes (e.g., cutting, coagulation, sealing), changing power level (e.g., voltage and/or current), duty cycle, terminating energy, and combinations thereof. This reading may be provided to the generator 40 which may continuously display the resulting strain readings as pressure imposed on the annular members 12a, 12b and tissue T. In some embodiments, the generator 40 may output an indication that a predetermined pressure has been reached. This indication may be used as one of the conditions in determining whether a tissue seal is complete.

Additionally, during an electrosurgical procedure, the characteristics of the tissue T may change such that the tissue T may resist movement of the electrode 30a differently. For example, charred tissue will be relatively tougher and have a tendency to resist movement. In some embodiments, the three-dimensional strain in the x, y, z coordinates, i.e., the ratio of the deformation of particular points within the electrode 30a relative to the original positioning of those points within the electrode 30a, will provide a mechanism to monitor and regulate the effects of the electrode 30a upon the tissue T.

Figure 7:
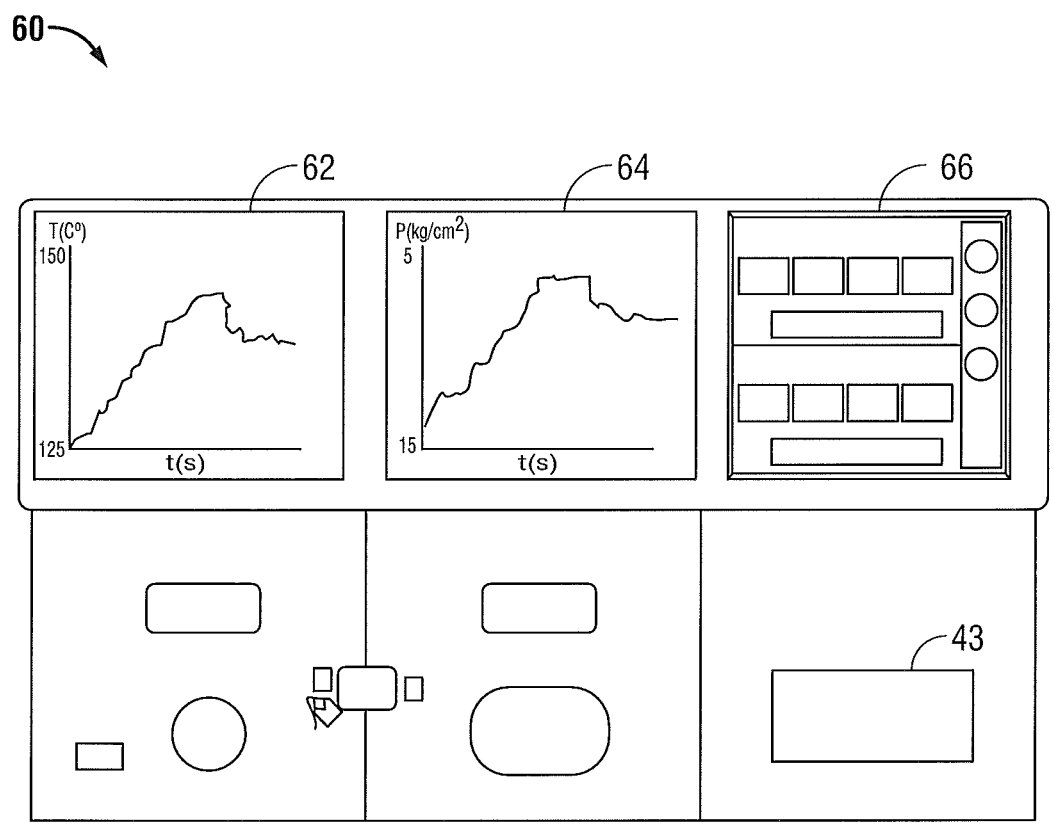
FIG. 7 is a front view of the display system of FIG. 1 according to the present disclosure.

Turning to FIG. 7, and as described above, and as described above, generator 40 may include a display system 60. Specifically, the display system 60 may be coupled to the interrogator 41a and/or the controller 41b (FIG. 1). Display system 60 may include a monitor or a graphic touchscreen display, as well as switches and illuminated indicators. Further, the controller 41b may be configured to execute algorithms for converting raw strain and temperature signals into one or more processed data, e.g., pressure measurements. In some embodiments, the display system 60 may include controls 66 allowing an operator to cycle through multiple display screens.

The display system 60 displays a graphical representation of the performance of finger-mountable annular members 12a, 12b or another surgical device. This graphical representation may include an image corresponding to the temperature and/or strain readings captured by the interrogator 41a and/or controller 41b. As shown, display system 60 may display a measured temperature or applied pressure by the annular members 12a, 12b over a time interval. Such a temperature gauge 62 may be measured over a range of, e.g., 125 to 150 degrees Celsius, and a pressure gauge 64 may be measured over a range of, e.g., 3 to 16 kg/cm$^2$. In some embodiments, the display system 60 may also display instantaneous pressure and/or temperature values. In further embodiments, display system 60 may display pressure and temperature in various real and graphical representations, such as bar graphs, which may be color-coded to represent the magnitude of pressure and temperature readings (e.g., red to represent high temperature and/or pressure, yellow to represent intermediate temperature and/or pressure, and green to represent low temperature and/or pressure, and combinations thereof). In this manner, display system 60 may provide a real-time pressure applied to tissue T by an operator as well as the thermal conditions at the tissue T. With this direct feedback, an operator, being in direct mechanical control of the electrodes 30a, 30b, may choose to alter or discontinue an electrosurgical procedure accordingly. Further, an operator may use the display system 60 to choose another surgical instrument or a differently-sized or configured finger-mountable annular member 12a, 12b with which to perform an electrosurgical surgical procedure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Although the foregoing disclosure has been described in some detail by way of illustration and example, for purposes of clarity or understanding, it will be obvious that certain changes and modifications may be practiced within the scope of the appended claims.

What is claimed is:

1. A surgical device, comprising:
    a pair of finger-mountable annular members, each of the finger-mountable annular members having an inner surface configured to be engaged with a finger, an outer surface, and an electrode disposed on the outer surface, the electrode configured to be coupled to an electrosurgical generator; and an optical member disposed on at least one of the pair of finger-mountable annular members having a first set of light transmitting properties corresponding to a first set of physical parameters of at least one of the finger-mountable annular members;

wherein at least one finger-mountable annular member is configured to transition to a second set of physical parameters being different from the first set of physical parameters, wherein the optical member is configured to transition from the first set of light transmitting properties to a second set of light transmitting properties, the second set of light transmitting properties corresponding to the second set of physical parameters, the second set of light transmitting properties being different from the first set of light transmitting properties.

2. The surgical device of claim 1, wherein the first and second sets of physical parameters are selected from the group consisting of temperature and mechanical strain.

3. The surgical device of claim 1, wherein the first and second sets of light transmitting properties include transmittance.

4. A surgical device comprising:

a first finger-mountable annular member;

a second finger-mountable annular member, each of the first and second finger-mountable annular members including an inner surface and an outer tissue engaging surface, the outer tissue engaging surfaces of the respective first and second finger-mountable annular members spaced away from each other in opposed relation;

an electrode disposed on each of the respective outer tissue engaging surfaces, each electrode configured to be coupled to an electrosurgical generator; and a sensor assembly operably coupled to at least one of the first finger-mountable annular member and the second finger-mountable annular member, the sensor assembly including:

an optical member;

a light source, the optical member configured to transmit light from the light source;

wherein a change in the transmission of light through the optical member corresponds to a changed condition of at least one of the first and second finger-mountable annular members.

5. The surgical device of claim 4, wherein each of the first and second finger-mountable annular members defines an opening therethrough.

6. The surgical device of claim 5, wherein the opening of each of the first and second finger-mountable annular members is configured to engage a mountable member.

7. The surgical device of claim 4, wherein the changed condition of at least one of the first and second finger-mountable annular members includes at least one of a change in temperature and a change in mechanical strain.

8. The surgical device of claim 4, wherein the optical member is associated with the first finger-mountable annular member, and a second optical member is associated with the second finger-mountable annular member.

9. The surgical device of claim 4, wherein the optical member is at least partially disposed within a portion of one of the first and second finger-mountable annular members.

10. The surgical device of claim 4, wherein the optical member includes a fiber Bragg grating.

11. The surgical device of claim 10, wherein the fiber Bragg grating reflects a first wavelength of light transmitted from the light source.

12. The surgical device of claim 11, wherein, in the changed condition, the fiber Bragg grating reflects a second wavelength of light from the light source, the second wavelength of light being different from the first wavelength of light.

13. The surgical device of claim 10, wherein the fiber Bragg grating includes a plurality of segments disposed in a periodic pattern.

14. The surgical device of claim 13, wherein each of the plurality of segments has a predetermined refractive index.

15. The surgical device of claim 4, wherein the optical member defines a length and has a refractive index that varies along the length of the optical member.

16. The surgical device of claim 4, wherein each of the electrodes is configured to pass a current therebetween.

* * * * *